United States Patent
Wong et al.

(10) Patent No.: US 10,041,881 B2
(45) Date of Patent: *Aug. 7, 2018

(54) NDIR GLUCOSE DETECTION IN LIQUIDS

(71) Applicant: Airware, Inc., Goleta, CA (US)

(72) Inventors: Jacob Y Wong, Goleta, CA (US); Thomas Campbell, Newbury Park, CA (US)

(73) Assignee: AIRWARE, INC., Goleta, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/785,829

(22) Filed: Oct. 17, 2017

(65) Prior Publication Data

US 2018/0143134 A1   May 24, 2018

Related U.S. Application Data

(63) Continuation-in-part of application No. 15/644,775, filed on Jul. 8, 2017, now Pat. No. 9,823,185, which is a continuation-in-part of application No. 15/594,418, filed on May 12, 2017, now Pat. No. 9,726,601, which is a continuation-in-part of application No. 15/444,136, filed on Feb. 27, 2017, now Pat. No. 9,678,000, which is a continuation-in-part of application No. 15/358,873, filed on Nov. 22, 2016, now Pat. No. 9,606,053.

(51) Int. Cl.
*G01N 21/35* (2014.01)
*G01N 33/49* (2006.01)
*G01N 21/59* (2006.01)

(52) U.S. Cl.
CPC ............. *G01N 21/59* (2013.01); *G01N 33/49* (2013.01); *G01N 2201/127* (2013.01)

(58) Field of Classification Search
CPC ........................ G01N 21/3504; G01N 33/49
See application file for complete search history.

(56) References Cited

U.S. PATENT DOCUMENTS

| | | | | |
|---|---|---|---|---|
| 6,509,567 B2 * | 1/2003 | Boudet | ................ | G01M 3/002 250/343 |
| 9,823,185 B1 * | 11/2017 | Wong | ................ | G01N 21/3504 |
| 2017/0265787 A1 | 9/2017 | Wong | | |

* cited by examiner

*Primary Examiner* — Mark R Gaworecki
(74) *Attorney, Agent, or Firm* — Roy L Anderson

(57) ABSTRACT

A glucose sensor measures glucose molecules in vivo through use of NDIR in which scattering noise is reduced and Absorption Interference Noise (AIN) is suppressed with a reflection technique. Electronics are used to provide an output of glucose concentration glucose in a liquid sampling matrix after it has been determined that a calibration curve is valid after signal processing is used to obtain average ratio values for reflected signal/reference channels and interference/reference channel obtained after a pulsed beam from signal, interference and reference sources is directed at an inclined angle to a normal of a spot of the liquid sampling matrix. The signal, interference and reference sources are each pulsed at a preselected frequency of at least N Hz which is sufficiently fast so that a given molecule of glucose or interfering molecule will not pass in and out of the liquid sampling matrix within the preselected frequency.

12 Claims, 12 Drawing Sheets

NDIR GLUCOSE DETECTION IN LIQUIDS

CROSS-REFERENCE TO RELATED APPLICATIONS

The present invention is a continuation-in-part application of U.S. Ser. No. 15/644,775 filed Jul. 8, 2017, which is a continuation-in-part application of U.S. Ser. No. 15/594,418 filed May 12, 2017, which was issued on Aug. 8, 2017 as U.S. Pat. No. 9,726,601, which is a continuation-in-part application of U.S. Ser. No. 15/444,136 filed Feb. 27, 2017, which was issued on Jun. 13, 2017 as U.S. Pat. No. 9,678,000, which is a continuation-in-part application of U.S. Ser. No. 15/358,873, filed Nov. 22, 2016, which was issued on Mar. 28, 2017 as U.S. Pat. No. 9,606,053, the disclosures of all of which are specifically incorporated herein by reference.

FIELD OF THE INVENTION

The present invention relates to an improved Non-Dispersive Infra-Red (NDIR) absorption method to detect molecules in the liquid phase alleviating weak absorption by the targeted molecules, debilitation of probing energy by liquid background absorption and suppression of both scattering and absorption interference noise (AIN) via a reflection detection technique.

BACKGROUND OF THE INVENTION

Non-Dispersive Infra-Red (NDIR) is a common measurement principle for detecting gases in the atmosphere. NDIR sensors utilize the principle that various gas molecules exhibit substantial absorption at specific wavelengths in the infrared radiation spectrum. The term "non-dispersive" as used herein refers to the apparatus used, typically a narrow-band optical or infrared transmission filter, instead of a dispersive element such as a prism or diffraction grating, for isolating for the purpose of measurement the radiation in a particular wavelength band that coincides with a strong absorption band of a gas to be measured.

The present invention is concerned with addressing problems arising from use of NDIR to detect molecules in a liquid medium, rather than in gas.

This and further objects and advantages will be apparent to those skilled in the art in connection with the figures and the detailed description of the invention set forth below.

SUMMARY OF THE INVENTION

The present invention is generally directed to an apparatus useful for determining a sample concentration of a chosen molecule M in a liquid phase through use of NDIR when at least one interfering molecule $M_J$ absorbs radiation at the signal wavelength used in the NDIR process. To compensate for absorption by one or more interfering molecules $M_J$, a third source, called an interference source is added. The signal source emits radiation at a wavelength which is within a first absorption band of the targeted molecule M, the interference source emits radiation at an interference wavelength which is within a second absorption band of said at least one interfering molecule $M_J$, and the reference beam emits radiation at a reference wavelength which is neutral and is not within either the first absorption band or the second absorption band. The signal source, the interference source and the reference source are each pulsed at a preselected frequency at least N Hz. (e.g., 10 KHz or greater with a duty factor of at least 10%) which is sufficiently fast so that a given molecule of the targeted molecule M or interfering molecule $M_J$ will not pass in and out of the liquid sampling matrix within the preselected frequency. Such a method will significantly suppress scattering noise when NDIR technique is used to detect molecules in the liquid phase rather than in the gaseous phase as disclosed in U.S. Pat. No. 9,606,053.

The signal, interference and reference sources are pulsed into a multiplexer and collimated into a pulsed beam which is directed at an inclined angle $(\eta/2-\theta_i)$ to the normal of a sample space containing the liquid at a spot. A detector detects infrared radiation as a pulsed signal after it emerges from the spot. Signal processing electronics is used to generate absorption coefficients $\alpha_{MNC}(\lambda_S)$ and $\alpha_{MNC}(\lambda_J)$ via measuring the transmittance of the targeted molecule in the liquid as a function of its concentration $C_N$ respectively at wavelengths $\lambda_S$ and $\lambda_J$. The condition of the liquid is designated by a parameter $\beta$ so that once it is analytically determined the calibration curve $F(C_N, \beta)$ for the targeted molecule in the liquid can be established in suppressing the Absorption Interference Noise (AIN) as disclosed in U.S. Pat. No. 9,726,601.

The object of the present invention is to further provide a functional and practical glucose sensor design via the use of a reflection sampling technique maintaining both the scattering noise and Absorption Interference Noise (AIN) suppression advantages for the measurement of glucose molecules in liquid in the presence of interfering molecules via NDIR.

DETAILED DESCRIPTION OF THE INVENTION

Figure 1:
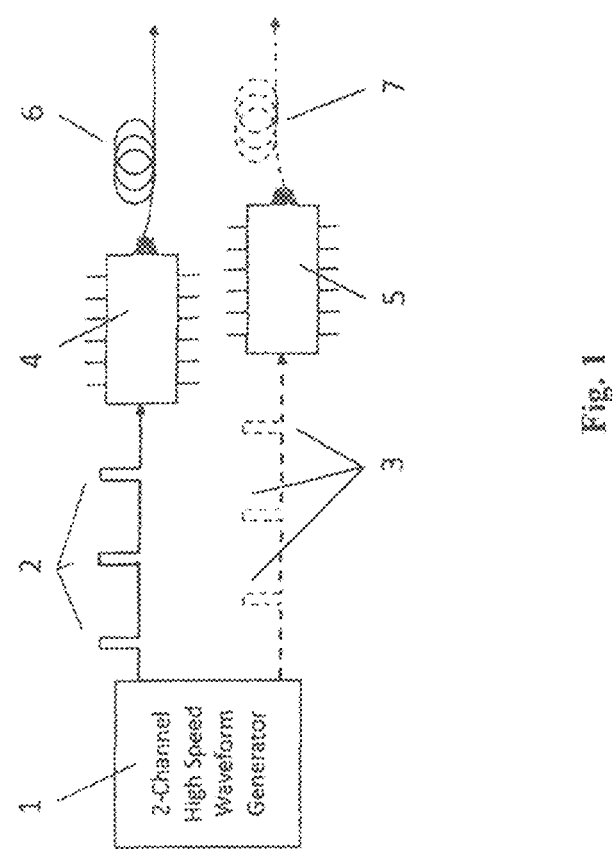
FIG. 1 illustrates how a Signal diode laser and the Reference diode laser are driven alternately and successively by a high speed waveform generator.

Because the present invention is concerned with addressing problems arising from use of NDIR to detect molecules in a liquid medium, rather than in gas, it is necessary to first review the inventive concepts that are disclosed in U.S. Pat. No. 9,606,053 (2017).

An NDIR sensor used to detect molecules in a gaseous phase typically utilizes an infrared source which sends radiation through a sample chamber to a detector which has a spectral filter that passes only radiation which coincides with the absorption band of the gas to be detected. The noise sources of such an NDIR sensor come mainly from the source, the detector and the temperature of the sensor environment.

Traditional NDIR technique uses a double beam configuration to reduce noise. A first channel, called a signal channel, uses an absorption wavelength chosen to detect a target gas and a first detector with a first filter coincident with the absorption of the target gas. A second channel, called a reference channel, uses a neutral wavelength (at which the target gas does not absorb) located close to the absorption wavelength with a second detector with a second filter which is in no way coincident with the absorption of the target gas. Because there are two different detectors, with radiation emanating from the same source, the signal and reference channels have two difference beam paths. The theory is that the signal channel is equally affected by all non-gas phenomena which might introduce noise to the signal channel, so by taking the ratio of the outputs of the two channels, namely the signal and reference channels, one can minimize all the noise-causing factors inevitably present in the sensor. So, ideally, only the presence of the target gas in the optical path will affect the ratio. The reason why the double beam configuration works so well in noise reduction is because particles in a gas phase are very well separated from one another with lots of space between them. Gas molecules typically move around very fast and have a molecular speed in the neighborhood of ~500 m/s. Consequently, at any particular instinct, only a very small number of molecules (including those that are targeted for detection) find themselves in between the source and the detectors. It is because of this particular particle environment that extraneous noise due to unwanted scattering is found to be very small and can be neglected when compared with other traditional noise sources.

If one wishes to use NDIR to detect molecules in liquid, a new source of noise will be introduced, namely, via scattering due to the difference between molecular densities in a gas phase versus that in a liquid phase. Whereas the scattering of source radiation by molecules lying between the source and the detectors is not a significant source of noise in a gaseous medium due to the large amount of free space between molecules, it can become a significant source of noise in a liquid phase where free space between molecules is greatly reduced.

Because of the different particle environment prevailing in the gas and liquid phases, the NDIR absorption technique for the detection of particles works well in the gas phase but not in the liquid phase. In order to solve this problem, the present invention takes an unprecedented approach to come up with a method and apparatus that makes the NDIR absorption technique work in the liquid phase very much like in the gas phase. The same double beam configuration of the traditional NDIR absorption technique is followed which includes the use of a second channel operating at a neutral wavelength just off that of the signal channel. By processing the ratio of the signal outputs from the two channels, namely the signal and the reference, some of the error-causing factors affecting the performance of the sensor will be eliminated, as expected, just as they are similarly eliminated when using the same technique in a gas phase. The additional and unique feature of the present method is to provide a sensor hardware configuration in which both the signal and the reference beams encounter almost exactly the same particle environment during measurement. This is accomplished by executing the following four steps.

Step one is to operate the signal beam and the reference beam separately, each with its own pulsed source. Furthermore, the sources of both beams are pulsed at the same and a very high frequency rate typically greater than 10 KHz with a duty factor around 20-25%. Because of this high pulse frequency requirement, only semiconductor LED and/or diode laser sources will be satisfactory.

Step two is to time the outputs of the signal and reference sources in such a way so that they are turned on alternately and sequentially one at a time, and, in an especially preferred embodiment, separated by no more than one-half of their pulsing period in time. Furthermore, the outputs of these two sources are optically combined via a multiplexer or other means that performs the same function so that both the signal and the reference beams physically traverse the same space of liquid matrix before being detected by a single infrared detector. The detector is required to have a response time fast enough to adequately generate the correct signal outputs from the rapidly incident radiation pulses from the signal and the reference beams.

Step three is to choose the wavelength of the signal and the reference channels. The choice of the wavelength for the signal channel has to be coincident with the absorption band of the target particle to be measured. The wavelength for the reference channel has to be neutral but just off the absorption and as close to it as possible but in no way coincident with it. This way of choosing the wavelength for the reference channel has to do with making sure that the same particle environment for purposes of scattering is almost the same for both the signal beam and the reference beam (if their wavelengths are almost the same). This is because of the fact that elastic scattering is a function of the wavelengths of the radiation in the incident beams.

Step four is processing the data received by the detector and explains how the calibration procedures are carried out in order to obtain the concentration level of the particles in the liquid. When the Signal beam and the Reference beam are alternately and successively pulsed at N Hz ($N>10^4$), a ratio value "R" is calculated for each generated Signal channel output and the corresponding Reference channel output, namely R=Signal/Reference. At the pulse rate of N Hz, there will be N such ratio values generated every second. For a preselected pulsing time period of "t", where "t" is in seconds, there will be N×"t" ratio values generated. The average value of R over this time period "t", namely $R_{ave}(t)$, is calibrated against the concentration of particles in the liquid. Thus the value of $R_{ave}(t)$ obtained by using a signal processing technique for analyzing the detector outputs yields the concentration level of the particles in the liquid.

The present invention takes advantage of the fact that although the density of molecules in the liquid phase is very high, the velocity of the molecules moving about in it is very slow, typically ~5 mm/sec. Thus, assuming that the cross-sectional area of the sampling matrix is of the order of a few $mm^2$, the time taken for molecules to move in and out of the sampling area many times is of the order of hundreds of milliseconds. Accordingly, if the measurement time between the Signal beam and the Reference beam is of the order of a few tenths of a millisecond, the particle environment traversed by both beams during the measurement can be considered as almost unchanged or substantially identical. In other words, since the particle environment for the Signal and the Reference channels during their respective measurement hardly changes when steps 1-4 described above for the liquid phase are executed, the phenomena of unwanted scattering should stay pretty much the same for both beams, with a resultant significant reduction and suppression of noise attributable to scattering arising from a liquid phase sampling environment.

FIGS. 1-4 schematically depict a specially designed apparatus that is used to implement the method of rendering the NDIR absorption technique workable in the liquid phase by suppressing unwanted scattering noise due to the presence of a large number of mobile particles in the liquid matrix between the source and the detector.

As shown in FIG. 1, a 2-channel high speed waveform generator 1 (>10 KHz) is employed to generate alternately and successively voltage pulses 2 and 3 to drive, respectively, Signal diode laser 4 and Reference diode laser 5. As shown in FIG. 1, the outputs of both diode laser 4 and diode laser 5 are interfaced respectively to optical fibers 6 and 7. The narrow spectral output of Signal diode laser 4 is selected to coincide with the absorption band of the target particle to be detected in the liquid matrix. But the narrow spectral output of Reference diode laser 5 is selected to be off but close to the absorption band of the target particle in the liquid matrix to be detected.

Figure 2:
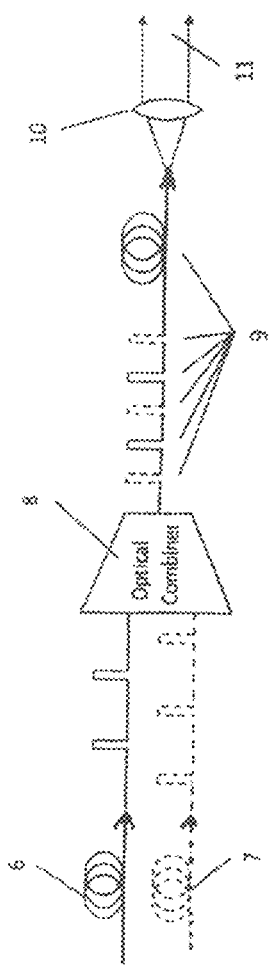
FIG. 2 illustrates how the outputs of the Signal diode laser and the Reference diode laser are combined into a single radiation beam alternately and successively representing both diode lasers via the use of an optical multiplexer.

FIG. 2 illustrates how outputs of the Signal laser beam 4 and Reference laser beam 5 are spatially combined into a single radiation beam before being focused onto the infrared detector. As shown in FIG. 2, output of the Signal laser beam 6 and output of the Reference laser beam 7 are combined in an optical multiplexer 8 to form a single radiation beam 9 before being collimated into a parallel beam 11 by collimating lens 10.

Figure 3:
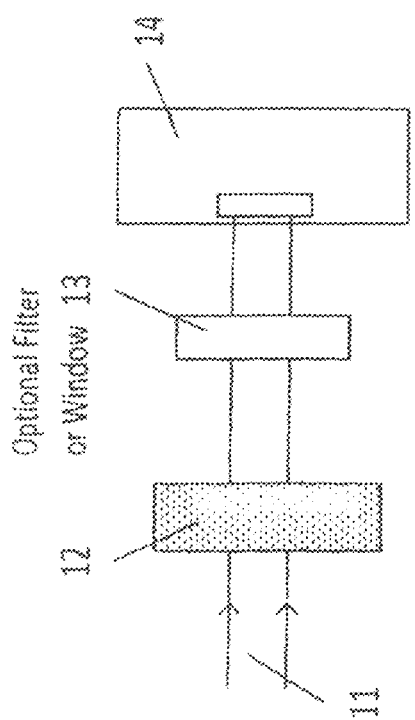
FIG. 3 illustrates the trajectory of the combined Signal and Reference diode laser beam to the infrared detector after passing through the sample chamber containing the liquid matrix and additional optional optical elements.

FIG. 3 illustrates how parallel radiation beam 11 (see FIG. 2) finds its way to the infrared detector. As shown in FIG. 3, single parallel beam 11 (which actually comprises both Signal laser beam 6 and Reference laser beam 7) being turned on alternately and successively by the 2-channel high speed waveform generator 1 of FIG. 1 first traverses sample chamber 12 containing the liquid matrix before being incident onto a TE-cooled infrared detector 14 after passing through an optional filter or window 13 for noise reduction (if needed).

Figure 4:
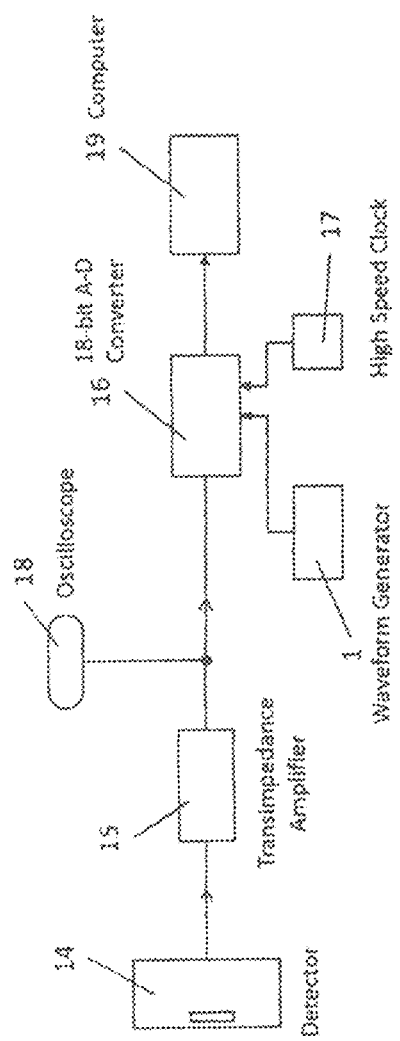
FIG. 4 illustrates the steps for transforming the analog infrared detector signal into digital data before inputting them into the computer for final data processing and analysis.

For signal processing as illustrated in FIG. 4, output of infrared detector 14 is first fed into a transimpedance amplifier 15 the output of which is inputted to an 18-bit Analog-to-Digital converter 16 triggered by waveform generator 1 (see FIG. 1) and a high speed clock 17. The analog signal can be monitored by an oscilloscope 18 before the digital signal is fed into a computer 19 for data analysis. Calculated ratio values are cross referenced to known compound concentration values. These compound concentration values can be reported individually to an output device such as a flat panel display. As values are collected over time, they can be plotted in a graphical format to illustrate trends over time. Running compound concentration values can be averaged over time, as one example, for smoother data tracking. Data output can be sent from the detector electronics by wired or wireless interfaces such as Bluetooth or WiFi standards to external devices.

Figure 5:
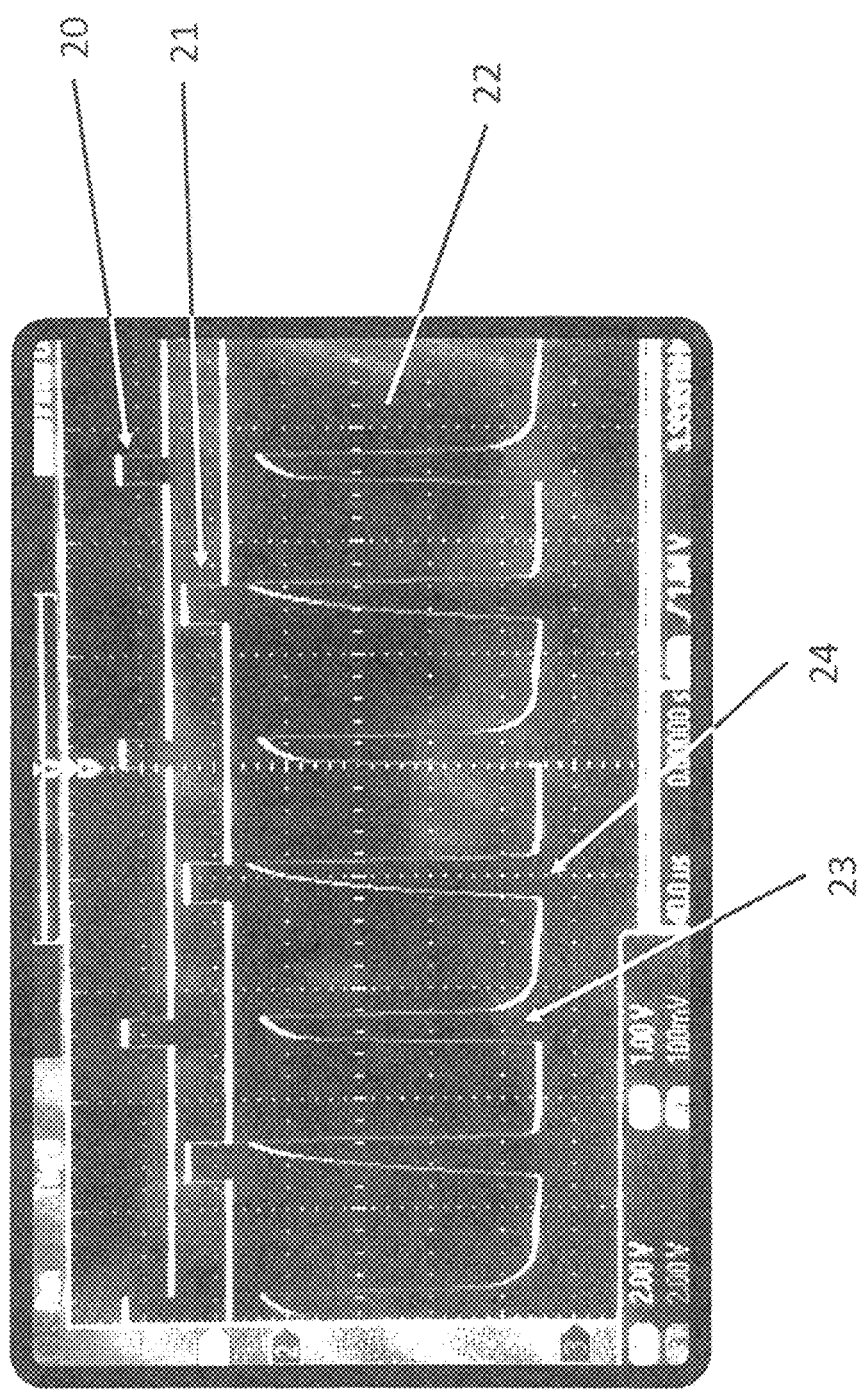
FIG. 5 illustrates the analog voltage outputs for driving the Signal and Reference diode lasers and the analog detector output for the combined laser beam prior to digitization.

FIG. 5 portrays the analog output as monitored by oscilloscope 18 (see FIG. 4). As shown in FIG. 5, the top two traces 20 and 21 of the oscilloscope display are voltage pulses 2 and 3 generated alternately and successively by high speed waveform generator 1 for driving respectively Signal diode laser 4 and Reference diode laser 5 (see FIG. 1). The bottom trace 22 of the oscilloscope display shows alternately the analog outputs of Signal laser beam 23 and Reference laser beam 24 from infrared detector 14 (see FIG. 3).

The processing of the digital data received by the computer from the infrared detector after initial data manipulation goes as follows. When both the Signal and Reference channels are pulsed at N Hz ($N>10^4$) for a measurement time period "t", where "t" is in seconds, there will be N×t Signal channel outputs and an equal number of Reference channel outputs generated by the infrared detector. A ratio value "R" is calculated for each generated Signal channel output and the corresponding Reference channel output, namely R=Signal output/Reference output. For the N×t ratio values of R calculated over the measurement time period 't', an average, namely $R_{ave}(t)$, is calculated. The calculated value of $R_{ave}(t)$ represents the measurement signal for the average concentration level of particles in the liquid in the time period "t". It is important to note that the signal to noise (S/N) for the measurement value of $R_{ave}(t)$ versus the average concentration level of particles in the liquid is a function of the value of the preselected time period "t". The longer the preselected measurement time period "t", the noise in the value of $R_{ave}(t)$ is smaller as there are more collected data to be averaged for the measurement value of it.

Figure 6:
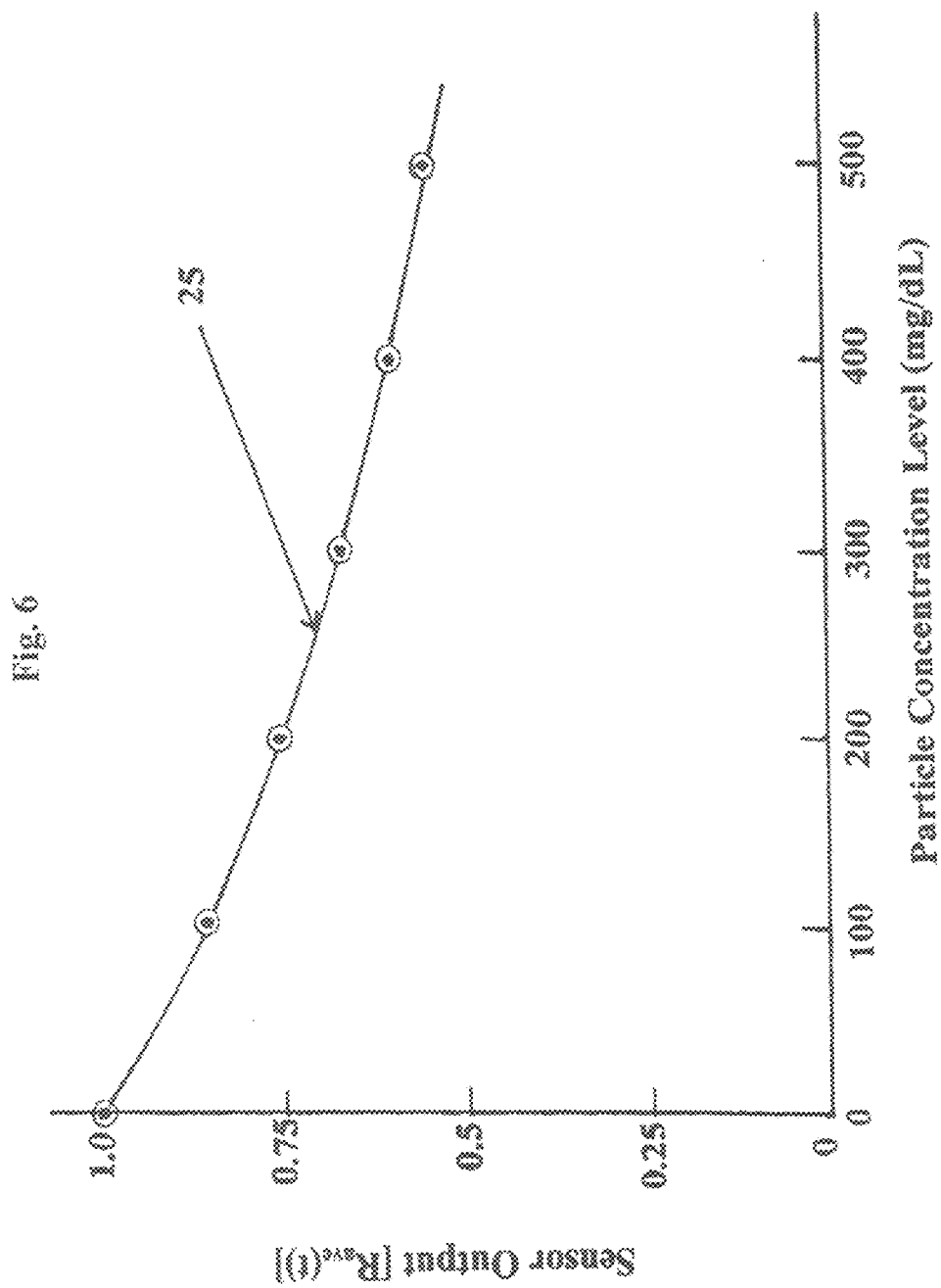
FIG. 6 illustrates a calibration curve for an NDIR liquid sensor depicting the sensor output ratio $R_{ave}(t)$ for the Signal and the Reference beams as a function of the particle concentration levels in liquid measured in milligram per 100 c.c. (mg/dL).

FIG. 6 shows graph 25 depicting the value of $R_{ave}(t)$ for a particular preselected measurement time period "t" as a function of the averaged particle concentration level "D" in the liquid measured in milligram per 100 cc (mg/dL). As can be seen in FIG. 6, the graph 25 is in essence the calibration curve of the particle concentration level for the NDIR liquid sensor. Such a calibration curve is attained by first selecting a liquid wherein different concentrations of particular particles in it are to be determined. Samples possessing different particle concentration levels in the liquid are then prepared. A measurement time period "t" is next selected for the calibration. By executing the four steps elucidated earlier for the measurement procedure, the values of $R_{ave}(t)$ are determined for each sample concentration in the liquid. The graph 25 as depicted in FIG. 6 portrays the value of $R_{ave}(t)$ as a function of the concentration levels of particles in the liquid with a preselected measurement time period "t".

Figure 7:
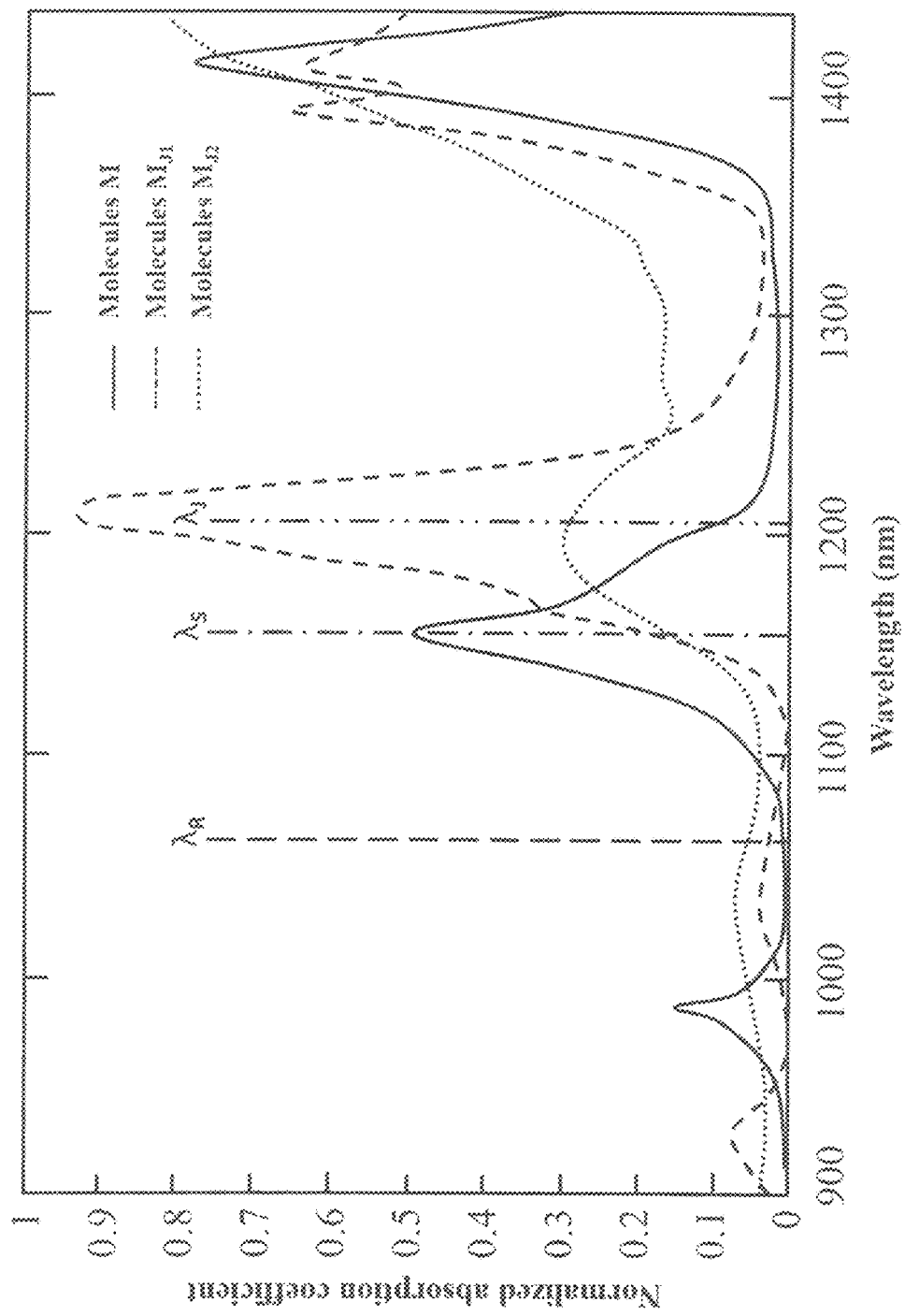
FIG. 7 shows the normalized absorption coefficients for targeted molecules M and interference molecules $M_J$ ($M_{J1}$ and $M_{J2}$) as a function of wavelength.

Now that the inventive concepts for suppressing scattering noise as disclosed in U.S. Pat. No. 9,606,053 have been reviewed, another noise source arises when NDIR is used to detect targeted molecules in liquid admixed with molecules having overlapping absorption bands as illustrated in FIG. 7. The inventive concepts for suppressing this new Absorption Interference Noise (AIN) as disclosed in U.S. Pat. No. 9,726,601 will now be reviewed. As shown in FIG. 7, the targeted molecule M has an absorption band at 1,150 nm ($\lambda_S$) and interfering molecules $M_J$ ($M_{J1}$ and $M_{J2}$) have an absorption band at ~1,200 nm ($\lambda_J$) and overlapping $\lambda_S$. In such a case, the interference molecules $M_{J1}$ and $M_{J2}$ will generate Absorption Interference Noise (AIN) impacting the transmittance measurement for targeted molecules M unless it is mitigated.

According to the Beer-Lambert law, the transmission of light at a particular wavelength $\lambda_S$ through a medium such as a liquid sample is expressed as:

$$I = I_0 e^{-OD}; \quad T = I/I_0; \quad \alpha = 1-T \text{ and } OD = \text{Log}_e(1/T) \quad (1)$$

where $I_0$ is the initial light intensity, I is the intensity after passing through the medium, T is the transmittance, a is the absorption coefficient and OD is the Optical Depth. When there is more than one type of molecule present in the liquid sample, the total absorption or composite transmittance at wavelength $\lambda_S$ through the sample is related to the summation of the individual optical depths of the molecules as follows:

$$OD(\lambda_S)_{total} = \text{Log}_e[1/T_{total}(\lambda_S)] = [C_1\alpha_1 + C_2\alpha_2 + \ldots] \times L \quad (2)$$

where $OD(\lambda_S)_{total}$ is the total optical depth, $C_i$ and $\alpha_i$ are respectively the molecular concentration and absorption coefficient of different molecules "i" and L is the common optical path or sample cell path length.

Equation (2) above implies that there exists a unique relationship among the quantities $T_M(\lambda_S)$, the transmittance; $C_M$, the concentration of targeted molecules M and $\alpha_M(\lambda_S)$, the absorption coefficient of the targeted molecules M in the liquid sample. Furthermore, the absorption coefficient of targeted molecules M and those of the admixed interfering molecules $M_J$ in liquid appear separately as individual parts in the measured total transmittance, namely:

$$1 - T_{total}(\lambda_S) = \alpha_M(\lambda_S) + \alpha_{MJ}(\lambda_S) \quad (3)$$

This knowledge is utilized to calibrate the concentration of the targeted molecules M versus the measured total transmittance of the liquid sample free from AIN noise.

Consider the case when targeted molecules M have an absorption band with Center Wavelength (CWL) located at $\lambda_S$ in a liquid sample and its concentration $C_M$ is to be determined optically via its absorption coefficient $\alpha_M(\lambda_S) = [1 - T_M(\lambda_S)]$, where $T_M(\lambda_S)$ is the transmittance measured at $\lambda_S$. Coexisting with the targeted molecule M are different types of molecules $M_J$ which have absorption bands overlapping wavelength $\lambda_S$. Under this situation, molecules $M_J$ will create Absorption Interference Noise (AIN) to the transmittance measurement at $\lambda_S$ for determining the absorption coefficient $\alpha_M(\lambda_S) = [1 - T_M(\lambda_S)]$ in order to arrive at the concentration of the targeted molecules M in the liquid.

By selecting and utilizing an additional near infrared Interference beam with wavelength $\lambda_J$ at a spectral location where an absorption band of one or more interfering molecules $M_J$ exists while at the same time overlapping $\lambda_S$, a calibration process can be developed effecting the suppression of the Absorption Interference Noise (AIN). Note that the interfering molecules $M_J$ must have some absorption at wavelength $\lambda$, and also have some overlapping absorption at $\lambda_S$. Also any additional number of admixed interfering molecules $M_X$ can be dealt with by utilizing additional NIR interference beam with wavelength $\lambda_X$.

By performing a transmittance measurement at $\lambda_J$ with a narrow radiation beam, only the absorption coefficient of interfering molecules $M_J$, namely $\alpha_{MJ}(\lambda_J) = 1 - T_{MJ}(\lambda_J)$ is being measured. The absorption coefficient of interfering molecules $M_J$ at $\lambda_S$, namely $\alpha_{MJ}(\lambda_S)$, is not affected. However, the measured absorption coefficients $\alpha_{MJ}(\lambda_S)$ and $\alpha_{MJ}(\lambda_J)$ are related to each other dependent upon the particular physical condition existing in the liquid sample. Their individual values depend only upon their absorption strength at the two different wavelengths $\lambda_J$ and $\lambda_S$. In other words one can express $$\alpha_{MJ}(\lambda_S) = \beta \times \alpha_{MJ}(\lambda_J) \quad (4)$$

where $\beta$ is a parameter defining a particular physical condition of the liquid sample and its value is less than unity when the absorption coefficient of molecules $M_J$ is stronger at wavelength $\lambda_J$ than at $\lambda_S$. Since both $\alpha_{MJ}(\lambda_S)$ and $\alpha_{MJ}(\lambda_J)$ refer to the same molecules $M_J$ but only measured at different wavelengths, the concentration of molecules $M_J$ in the liquid sample cannot change the value of $\beta = \alpha_{MJ}(\lambda_S)/\alpha_{MJ}(\lambda_J)$. However, the value of $\beta$ does depend on the physical condition of the liquid sample. When the values of $\alpha_{MJ}(\lambda_J)$ and $\beta$ are known, one can calculate $\alpha_{MJ}(\lambda_S)$ by using Equation (4) above. But if $\alpha_{MJ}(\lambda_S)$ is known, $\alpha_M(\lambda_S)$ can now be determined from Equation (3) through the measurement of $T_{total}(\lambda_S)$ independent of the presence of $M_J$ and its concentration in the liquid sample. Under this circumstance the Absorption Interference Noise (AIN) caused by the presence of $M_J$ in the liquid sample will be significantly suppressed or eliminated when the concentration of molecules M in the liquid sample is measured.

The implementation of this calibration methodology suppressing Absorption Interference Noise (AIN) can now be divulged in more details as follows. According to the Beer-Lambert law as stated in Equation (1) above, different concentrations $C_N$ of molecules M in a liquid sample at a particular physical condition defined by "$\beta$" can be expressed as follows:

$$1 - T_{MC1}(\lambda_S) = \alpha_{MC1}(\lambda_S) + \beta \times \alpha_{MJC1}(\lambda_J) \ldots \text{ for concentration } C_1 \quad (5)$$

$$1 - T_{MC2}(\lambda_S) = \alpha_{MC2}(\lambda_S) + \beta \times \alpha_{MJC2}(\lambda_J) \ldots \text{ for concentration } C_2$$

$$\vdots$$

$$1 - T_{MCN}(\lambda_S) = \alpha_{MCN}(\lambda_S) + \beta \times \alpha_{MJCN}(\lambda_J) \ldots \text{ for concentration } C_N$$

Where $T_{MCN}(\lambda_S)$ is the total transmittance measured at $\lambda_S$ of molecules M in a liquid sample with concentration $C_N$, $\alpha_{MCN}(\lambda_S)$ is the absorption coefficient at $\lambda_S$ of molecules M in the liquid sample with concentration $C_N$, $\alpha_{MJCN}(\lambda_J)$ is the absorption coefficient at $\lambda_J$ of interfering molecules $M_J$ and molecules M with concentration $C_N$ in the liquid sample and "$\beta$" is a constant parameter characterizing the physical condition of the liquid sample as defined in Equation (4) above. One can alternately express Equation (5) above as follows:

$$\alpha_{MCN}(\lambda_S) = 1 - T_{MCN}(\lambda_S) - \beta \times \alpha_{MJCN}(\lambda_J) = F(C_N, \beta) \quad (6)$$

with $C_N$ denoting different concentration of molecules M in the liquid sample. For every $C_N$, both $T_{MCN}(\lambda_S)$ and $\alpha_{MJCN}(\lambda_J) = 1 - T_{MCN}(\lambda_J)$ are respectively measurable at wavelengths $\lambda_S$ and $\lambda_J$. But since the parameter $\beta$ depends upon the unknown physical condition of the sampling liquid, the absorption coefficient $\alpha_{MCN}(\lambda_S)$ of molecules M in a liquid sample can only be calibrated as a function of its $C_N$ and "$\beta$", namely $F(C_N, \beta)$ as shown in FIG. 8.

Figure 8:
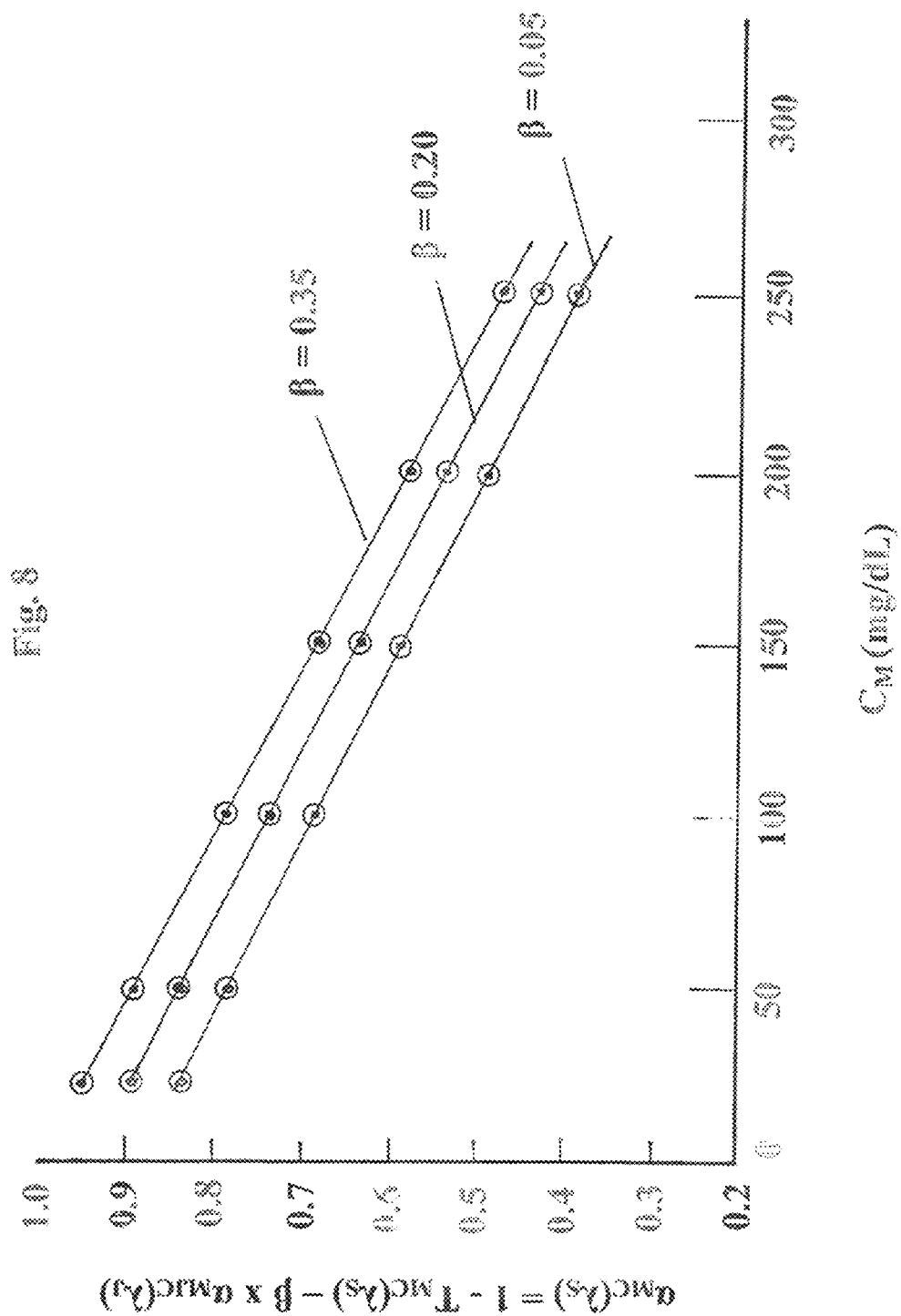
FIG. 8 shows the set of calibration curves $F(C_M, \beta)$ for concentration of molecules M as a function of the absorption coefficient without the presence of Absorption Interference Noise (AIN) caused by interfering molecules.

The family of calibration curves $F(C_N, \beta)$, namely $\alpha_{MCN}(\lambda_S)$ versus different $C_N$ and designated by different physical condition parameter "$\beta$" of the liquid sample, as shown in FIG. 8, is first obtained by calibrating the concentration $C_N$ of molecules M against the measured values of $T_{MCN}(\lambda_S)$ and $\alpha_{MJCN}(\lambda_J)=1-T_{MCN}(\lambda_J)$ respectively at $\lambda_S$ and $\lambda_J$ carrying a specific value of "$\beta$"=0.2 arbitrarily designated as the physical condition of the liquid sample. The family of calibration curves is then generated with this measured calibration curve with different assigned values of "$\beta$" representing different physical conditions of the liquid sample as shown in FIG. 8. Note that the family of calibration curves can be constructed from the first measured calibration curve with as fine a scale of $\beta$ as needed. Since the physical condition of the liquid sample represented by the value of "$\beta$" is unknown, its value must first be correctly determined before the corresponding calibration curve can be used for subsequent measurements of the concentration of molecules M in the liquid sample. This is accomplished by measuring the values of $T_{MCN}(\lambda_S)$ and $\alpha_{MJCN}(\lambda_J)=1-T_{MJCN}(\lambda_J)$ for a particular liquid sample containing a known concentration $C_N$ of molecules M and selecting the calibration curve with the $\beta$ value in FIG. 8 that yields the best $C_N$ value. The calibration curve so selected will be the calibration curve for subsequent measurements for the concentration of molecules M in the liquid sample without the influence of the Absorption Interference Noise (AIN) even in the presence of an unknown amount of interfering molecules $M_J$ in it.

Note that the correct value of $\beta$ can be checked prior to the use of a specific selected calibration curve in FIG. 8 for a sensor by comparing the presently measured value of $\alpha_{MJCN}(\lambda_J)=1-T_{MJCN}(\lambda_J)$ with that of the previously stored in the sensor. The constancy of this value implies that the physical condition of the liquid sample has not changed and the specifically chosen calibration curve in FIG. 8 is valid for use for the sensor.

It is well known that water, which is the main components of most common liquid, strongly absorbs radiation with wavelength lying in the near infrared (NIR) spectral region. The use of NDIR passing through absorption sampling technique to detect molecules in liquids with absorption bands lying in the NIR spectral region as described previously suffers greatly in Signal-to-Noise (S/N) performance because of the reduction in available probing energy from the radiation source to the detector due to water absorption. Furthermore, the use of the NDIR passing through absorption sampling technique for the design of wrist watch style molecular concentration sensors is inept and inefficient.

Figure 9:
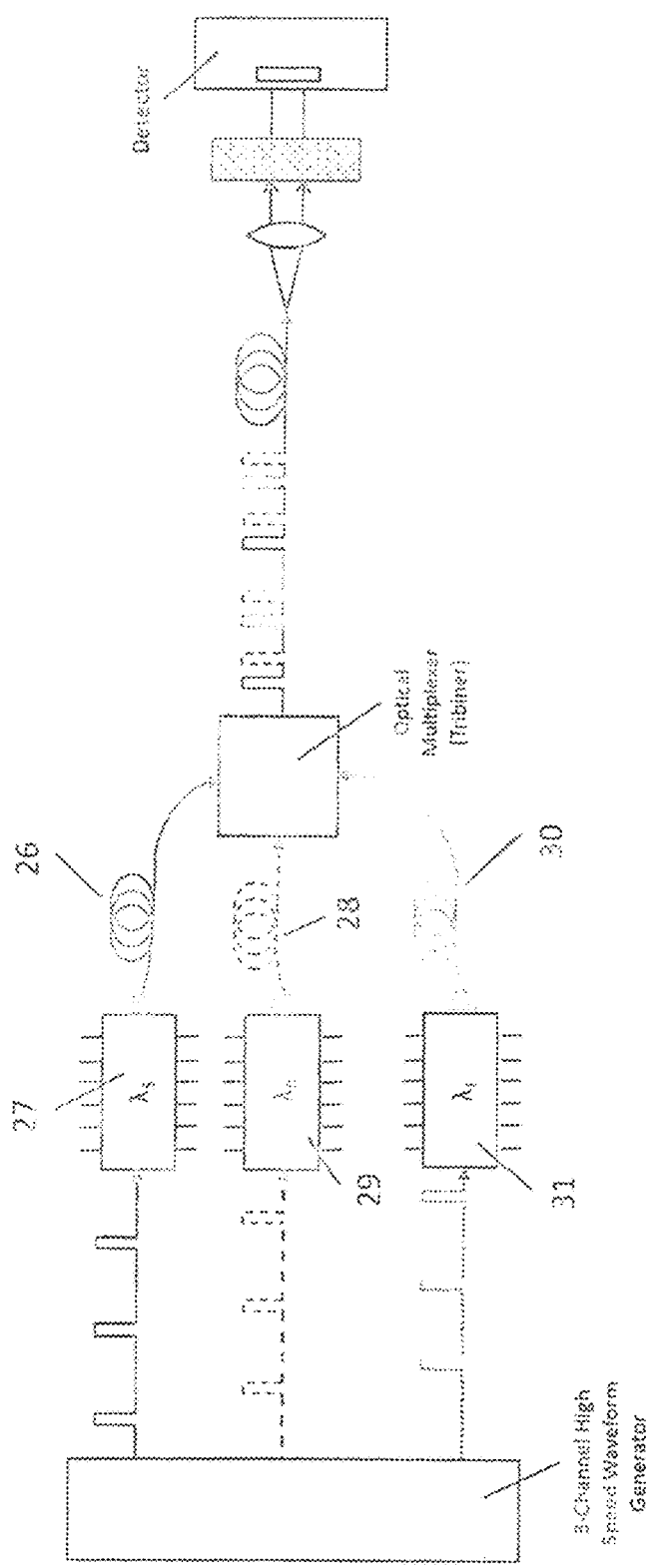
FIG. 9 shows an optical setup illustrating how a Signal diode laser, a Reference diode laser and an Interference diode laser are driven alternately and successively by a 3-channel high speed waveform generator.

Now that the inventive concepts for measuring molecules in liquids using NDIR passing through absorption sampling technique for suppressing both the scattering noise and Absorption Interference Noise (AIN) as disclosed respectively in U.S. Pat. Nos. 9,606,053 and 9,726,601 have been reviewed, a new NDIR reflection sampling technique to detect molecules in liquids alleviating the water absorption and sensor inept design problems will now be reviewed. FIG. 9 is an optical setup illustrating how a Signal diode laser, a Reference diode laser and an Interference diode laser are driven alternately and successively in groups of two by a 3-channel high speed waveform generator. As shown in FIG. 9, output 26 of Signal diode laser 27 is driven alternately and successively with output 28 of Reference diode laser 29 as a pair; meanwhile output 30 of Interference diode laser 31 is driven alternately and successively with output 28 of Reference diode laser 29 as another pair. This is carried out in order that the transmittance can be measured at $\lambda_S$ at essentially the same time as it is measured at $\lambda_J$, so that both will have essentially the same scattering noise reduction advantage. The rest of the optical and electronic processing system setup for a three diode laser system to suppress both scattering noise and AIN noise is the same as the two diode laser system disclosed in U.S. Pat. No. 9,606,053 (2017).

Figure 10:
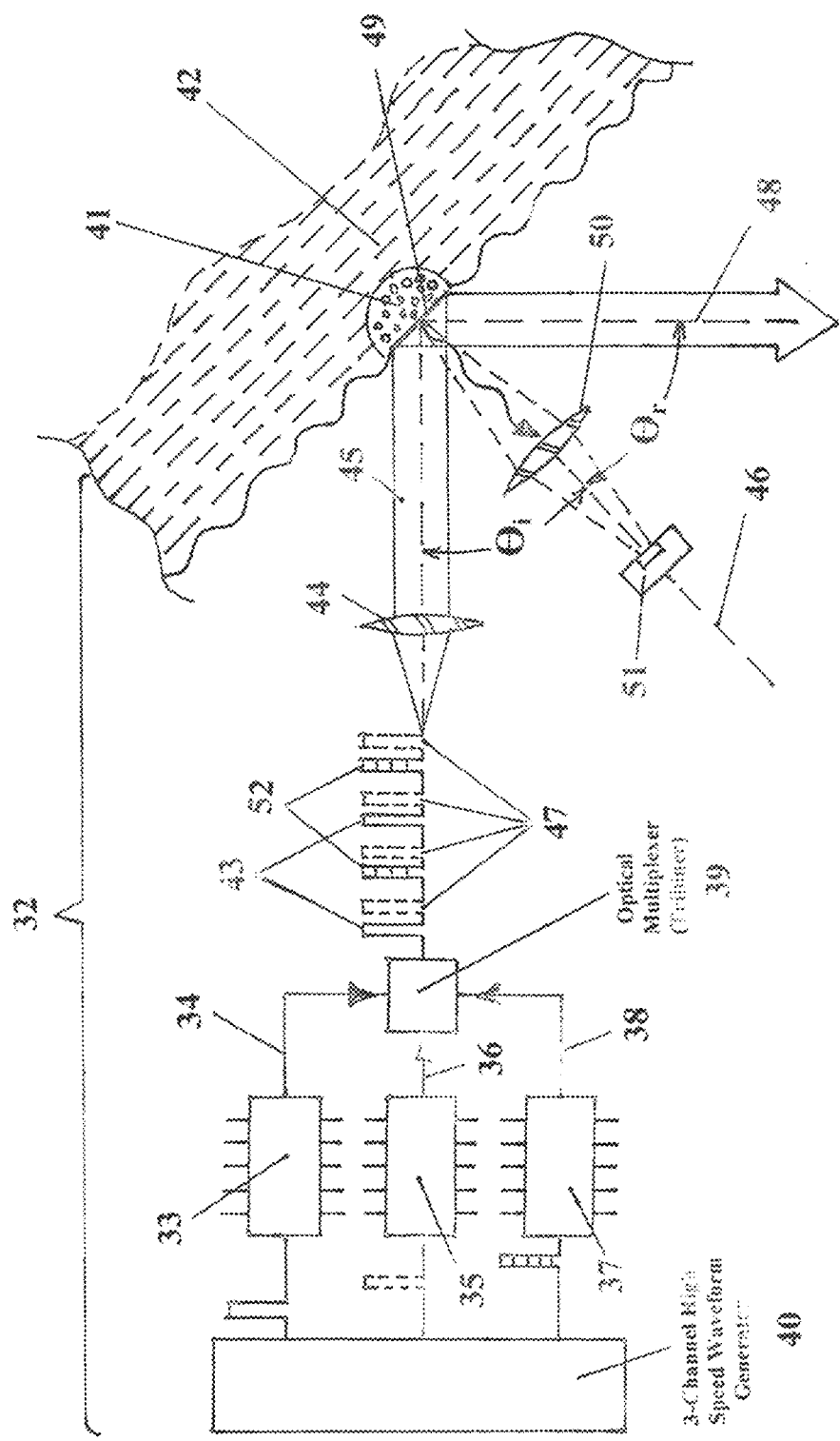
FIG. 10 shows the design of an optical reflection system according to the present invention for determining the concentration of a targeted molecule in a liquid sample.

FIG. 10 depicts schematically a specially designed optical system 32 using a NDIR reflection sampling technique to detect molecules in a liquid medium via measuring its transmittance "T" [see Equation (1) above]. Such an optical system is capable of suppressing both the scattering noise and the Absorption Interference Noise (AIN) that are commonly encountered in the use of NDIR absorption technique for such a measurement. FIG. 10 illustrates how a Signal diode laser ($\lambda_S$) 33, a Reference diode laser ($\lambda_R$) 35 and an Interference diode laser ($\lambda_J$) 37 are driven alternately and successively into groups of two, namely (Signal laser 33 and Reference laser 35 as a pair) and (Interference laser 37 and Reference laser 35 as another pair) by a 3-channel high speed waveform generator 40. As shown in FIG. 10, the output 34 of Signal diode laser 33 is driven alternately and successively with output 36 of Reference diode laser 35 as a pair optically coupled to a 3-channel multiplexer (tribiner) 39. Meanwhile the output 38 of Interference diode laser 37 is driven alternately and successively with output 36 of Reference diode laser 35 as another pair optically coupled into the same tribiner 39.

Consider first the transmittance measurement of a liquid sample located at spot 41 of sample area 42 (see FIG. 10) at wavelength $\lambda_S$. The output 34 of Signal laser diode 33 is being coupled into an optical multiplexer (Tribiner) 39 the output of which 43 is then collimated by lens 44 into a narrow beam 45 having a diameter of ~1.0 mm before impinging at spot 41 of the sample area 42 at an inclined angle $\theta_i$ to the sample area normal 46. The output 36 of Reference diode laser 35 is being coupled into the same optical multiplexer (Tribiner) 39 the output of which 47 is then collimated by lens 44 into a narrow beam 45 having a diameter of ~1.0 mm before impinging at the same spot 41 of sample area 42 at an inclined angle $\theta_i$ to the sample area normal 46. Both the Signal beam ($\lambda_S$) and the Reference beam ($\lambda_R$) are sequentially and alternately pulsed and specularly reflected at the same spot 41 of sample area 42 into beam 48 which is not being used in the current invention. Both the Signal beam ($\lambda_S$) and the Reference beam ($\lambda_R$) penetrate a small distance into the sample area 42 where transmission, absorption and reflections of the incident radiations take place before they emerge from the sample area surface 49 at spot 41. The radiation coming out from spot 41 is collected by lens 50 onto detector 51 for signal processing. This optical measurement technique for the Signal beam ($\lambda_S$) and the Reference beam ($\lambda_R$) described herein enables the suppression of the scattering noise in the measured transmittance value at wavelength $\lambda_S$ as disclosed in U.S. Pat. No. 9,606,053 (2017).

Consider now the transmittance measurement of a liquid sample located at spot 41 of sample area 42 (see FIG. 10) at wavelength $\lambda_J$. The output 38 of Interference laser diode 37 is being coupled to an optical multiplexer (Tribiner) 39 the output of which 52 is then collimated by lens 44 into a narrow beam 45 having a diameter of ~1.0 mm before impinging at spot 41 of the sample area 42 at an inclined angle $\theta_i$ to the normal 46 of sample area 42. The output 36 of Reference diode laser 35 is coupled to the same optical multiplexer (Tribiner) 39 the output of which 47 is then collimated by lens 44 into a narrow beam 45 having a diameter ~1.0 mm before impinging at the same spot 41 of sample area 42 at an angle $\theta_i$ to the normal 46 of sample area 42. Both the Interference beam ($\lambda_J$) and the Reference beam ($\lambda_R$) penetrate a small distance into the sample area 42 where transmission, absorption and reflections of the radiation beams take place before radiation emerges from the sample area surface 49 at spot 41. The radiation coming out from spot 41 (which does not need to be an outside surface spot, but may be located beneath another layer or substance) is collected by lens 50 onto detector 51 for signal processing. This optical measurement technique described herein for the Interference beam ($\lambda_J$) and the Reference beam ($\lambda_R$) enables the suppression of the scattering noise in the measured transmittance value at wavelength $\lambda_J$ as disclosed in U.S. Pat. No. 9,606,053 (2017).

The signal processing procedure for suppressing both scattering noise and AIN noise as described above using a NDIR reflection sampling technique for dealing with a liquid sample in which targeted molecules are admixed with molecules of some other kinds overlapping the same absorption band signature is exactly the same as that disclosed in U.S. Pat. No. 9,726,601 for using a NDIR passing through absorption sampling technique.

Now that a more efficient NDIR reflection sampling technique along with inventive concepts for suppressing both scattering noise and Absorption Interference Noise (AIN) are reviewed, these principles set forth hitherto will now be expounded with reference to the design of a non-invasive sensor for determining glucose concentration in blood or interstitial fluid. As disclosed earlier in U.S. Pat. Nos. 9,678,000 and 9,726,601, glucose has an overtone absorption band located in the near infrared (NIR) spectral region at 1,150 nm which can be used as the center wavelength $\lambda_S$ for the Signal beam. This absorption band is desirable because it has a water absorption coefficient of no greater than ~1.0 cm$^{-1}$ thus minimizing the debilitation of the probing radiation from the source. The wavelength at 1,060 nm, where there is no glucose or other molecule absorption, can be used as the center wavelength $\lambda_R$ for the Reference beam. Finally for certain interfering molecules coexisting with glucose in blood or interstitial fluid like lipids and collagens, these molecules have absorption at ~1,210 nm and overlapping the signal wavelength $\lambda_S$ of glucose at 1,150 nm. Therefore the wavelength at 1,210 nm can be chosen as the center wavelength $\lambda_J$ for the Interference beam.

Figure 11:
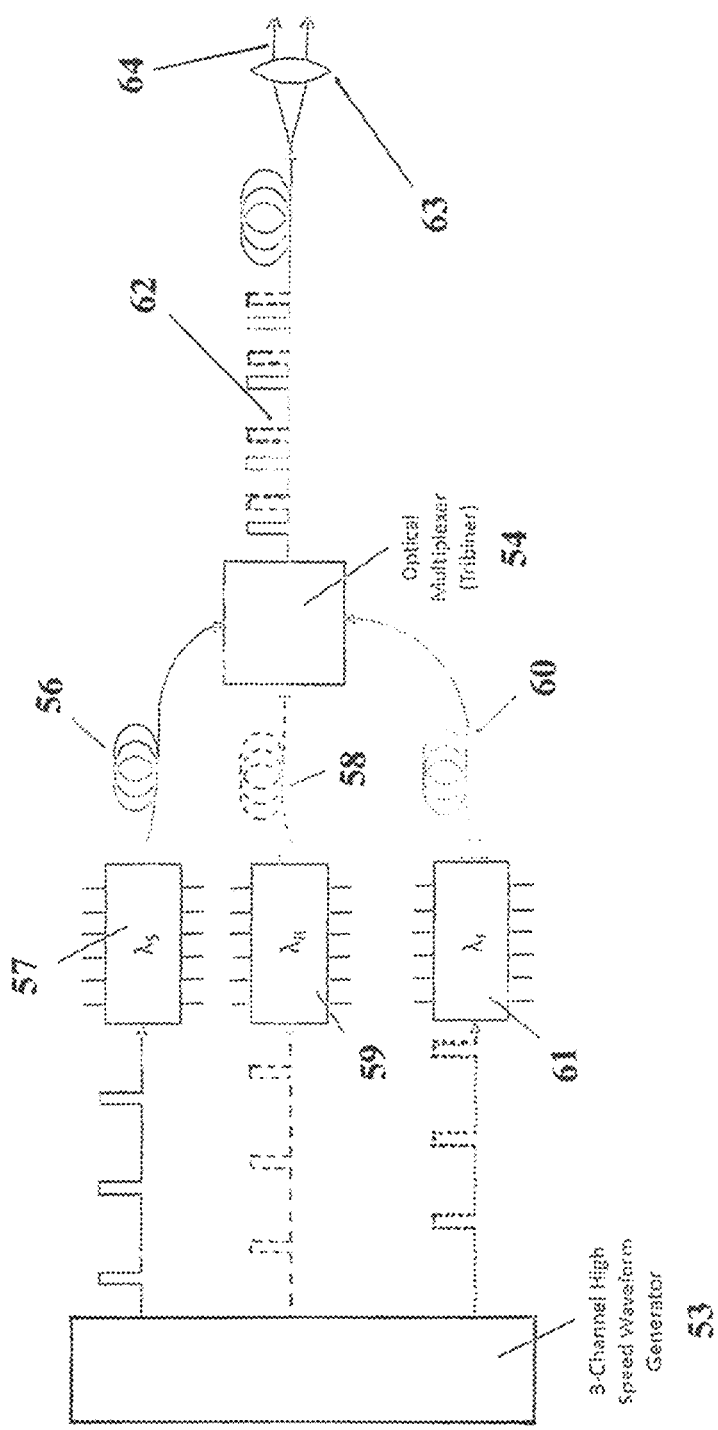
FIG. 11 shows an optical setup illustrating how a Signal diode laser, a Reference diode laser and an Interference diode laser are driven alternately and successively by a 3-channel high speed waveform generator and fiber-coupled into a single radiation beam by an optical multiplexer.

FIG. 11 shows an optical setup illustrating how a Signal diode laser emitting at $\lambda_S$=1,150 nm, a Reference diode laser emitting at $\lambda_R$=1,060 nm and an Interference diode laser emitting at $\lambda_J$=1,210 nm are driven alternately and successively in groups of two by a 3-channel high speed waveform generator 53. As shown in FIG. 11, output 56 of Signal diode laser 57 is driven alternately and successively with output 58 of Reference diode laser 59 as a pair and are optically coupled to a 3-channel multiplexer (tribiner) 54. Meanwhile output 60 of Interference diode laser 61 is driven alternately and successively with output 58 of Reference diode laser 59 as another pair and are also optically coupled to tribiner 54. The process of operating the three diode lasers in this manner is to make sure that the transmittance of glucose coexisting with other interfering molecules in blood or interstitial fluid can be measured at wavelengths $\lambda_S$ and $\lambda_J$(with $\lambda_R$ as reference) at essentially the same time so that scattering noise and Absorption Interfering Noise (AIN) faced by both measurements are essentially the same. As shown in FIG. 11 the outputs of the Signal laser beam ($\lambda_S$), the Reference laser beam ($\lambda_R$) and the Interference laser beam ($\lambda_J$) are combined in the 3-channel multiplexer (tribiner) 54 to form a single fiber coupled radiation beam 62 collimated by lens 63 into a narrow parallel laser beam 64 before being further processed.

The strategic selection of the wavelengths for the Signal ($\lambda_S$), Reference ($\lambda_R$) and Interference ($\lambda_J$) beams, respectively at 1,150 nm, 1,060 nm and 1,210 nm, and the manner they are driven and processed for measuring the transmittance of blood or interstitial fluid samples are crucial to the implementation of the current inventive concept to the successful non-invasive measurement of glucose concentration in blood or interstitial fluid coexisting with lipids, collagens etc. circumventing the crippling effects of scattering noise and Absorption Interference Noise (AIN). A further object of the present invention is to provide a specially designed reflection sensor system capable of achieving the reduction of both scattering noise and Absorption Interference Noise (AIN) for the non-invasive concentration measurement of glucose molecules in blood or interstitial fluid in the presence of interfering molecules like lipids, collagens etc. The present invention further takes full advantage of today's advanced technologies in NIR laser sources, Indium Gallium Arsenide (InGaAs) photodetectors, MicroElectro-Mechanical Systems (MEMS), ASICs with complex signal processing circuitries, cloud base creative software and miniature packaging techniques utilizing nanoCHIP structures in order to come up with a viable and practical non-invasive blood glucose monitor capable of relieving the painful daily finger sticks needed by persons with diabetes.

Figure 12:
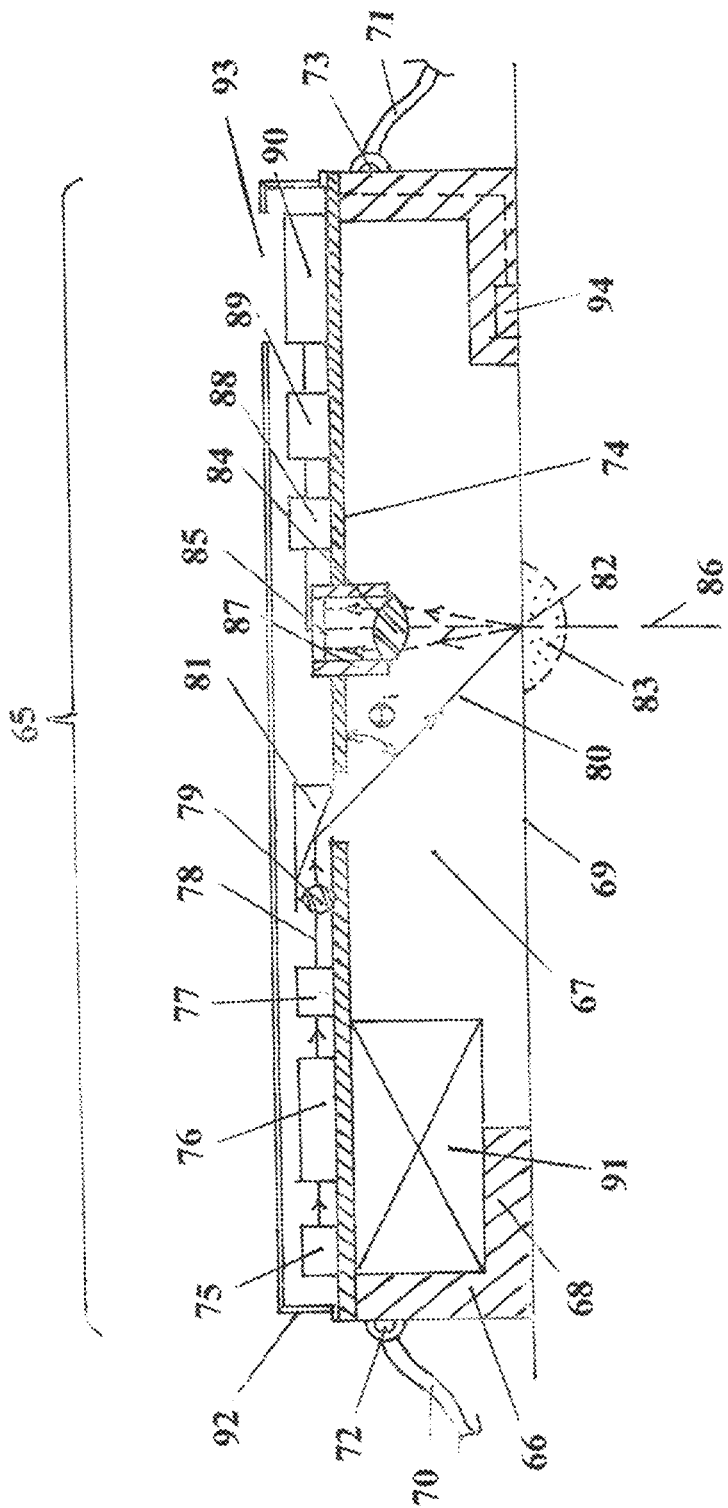
FIG. 12 shows the design of an efficient and practical reflection sensor according to the present invention for determining the concentration of glucose molecules in liquids.

FIG. 12 depicts schematically a specially designed optical sensor 65 using a NDIR reflection sampling technique as disclosed in U.S. Ser. No. 15/644,775 filed Jul. 8, 2017 to detect glucose concentration in blood or interstitial fluid via measuring its total transmittance $T_{MCN}(\lambda_S)$ and $T_{MCN}(\lambda_J)$ respectively at wavelength $\lambda_S$ and $\lambda_J$(with $\lambda_R$ as reference) where $T_{MCN}(\lambda_S)=1-\alpha_{MCN}(\lambda_S)$ and $T_{MCN}(\lambda_J)=1-\alpha_{MCN}(\lambda_J)$. Quantities $\alpha_{MCN}(\lambda_S)$ and $\alpha_{MCN}(\lambda_J)$ are the absorption coefficient of blood or interstitial fluid measured respectively at wavelengths $\lambda_S$ and $\lambda_J$(with $\lambda_R$ as reference) having a glucose concentration value of $C_N$ coexisting with an unknown amount of lipids and collagens in it.

As shown in FIG. 12, the optical sensor 65 with dimensions ~3 cm×6 cm×1 cm has a thin-walled open top rectangular frame 66 with a smaller open bottom 67 defined by surrounding edge 68 which enables sensor 65 to rest on a surface 69 like that of human skin. Two straps 70 and 71, one on each of the two short sides of the frame 66 and held respectively by hinges 72 and 73. Straps 70 and 71 can be used to fasten sensor 65 onto the human wrist like a watch or onto anywhere along the upper arm of a human subject.

All the optical components and electronic circuitries of sensor 65 are mounted physically or via solder on printed circuit board (PCB) 74 located above the box frame 66 and serving as its top. All the components of the optical setup for sensor 65 as described earlier in detail in FIG. 11 are located on the left hand side of PCB 74 as shown. Starting out from the left hand side of PCB 74, 75 is the 3-channel high speed waveform generator followed by the 3-channel electronic driver moduli 76 for the Signal, Reference and Interference lasers respectively with output wavelengths of $\lambda_S$, $\lambda_R$ and $\lambda_J$. 77 is the 3-channel multiplexer or tribiner whose output is fiber-coupled into a single radiation beam 78. Beam 78 is collimated by lens 79 into a parallel beam 80 before being reflected by mirror 81 towards the spot 82 of the sampling area 83.

The parallel beam 80 impinges at spot 82 of the sampling area 83 at an inclined angle $\theta_i$ to the PCB 74. Beam 80 penetrates a small distance into the sample area 83 at spot 82 where transmission, absorption and reflections take place to the impinging beam before it emerges from the sampling area 83 at spot 82. The radiation coming out from spot 82 is collected by lens 84 onto detector 85 for signal processing. The axis of both lens 84 and detector 85 are aligned with the normal 86 of the sampling area 83 at spot 82. Both are mounted in a special housing 87 secured on PCB 74 facing the sampling area 83 at spot 82.

Processing electronics including the control and operation of the 3-channel high speed waveform generator 75 and the 3-channel laser driver moduli 76 are located on the right hand side of PCB 74. It is the software and processing circuits installed inside the CPU of ASIC 88 and supported by memory chip 89 (see FIG. 12) that control the logic and sequence of transmittance measurements for the Signal ($\lambda_S$) and Interference ($\lambda_J$) beams in coordination with the Reference beam ($\lambda_R$). The glucose measurement results (immediate and/or trending) along with operational instructions and controls for sensor 65 are provided by a display chip 90. A temperature transducer 94 used to monitor the temperature of the surface 69 contacted by sensor 65 is located at the bottom edge 68 of sensor frame 66 and electrically connected to PCB 74. A battery 91 is housed inside the sensor frame 66 below the PCB 74 to provide power to the entire sensor 65. Finally all the components mounted on PCB 74 are protected by a cover 92 except for the display chip 90 where there is an opening 93 above it.

While the invention described herein with reference to a preferred embodiment, this embodiment has been presented by way of example only, and not to limit the scope of the invention. Additional embodiments thereof will be obvious to those skilled in the art having the benefit of this detailed description. Further modifications are also possible in alternative embodiments without departing from the inventive concept.

What is claimed is:

1. An apparatus for determining a concentration of a targeted molecule M within a given time period in a liquid sampling matrix in which at least one interfering molecule $M_J$ coexists with the targeted molecule, comprising:
   a signal source;
   an interference source;
   a reference source;
   a multiplexer and a collimator configured to pulse infrared radiation from the signal source, the interference source and the reference source into a pulsed beam which is directed at an inclined angle ($\theta_i$) to a normal of a spot of the liquid sampling matrix;
   a detector configured to detect infrared radiation after it emerges from the spot as a pulsed signal and reference channel output and a pulsed interference signal and reference channel output from the pulsed beam after it penetrates into the spot;
   signal processing for:
      obtaining an average ratio value of $R_{ave}(t)$ for a first preselected period of time ("t") from the pulsed signal and reference channel output, where $R_{ave}(t)$ =signal channel/reference channel output for the first preselected period of time, and
      obtaining an average ratio value of $R_{Jave}(t_2)$ for a second preselected period of time ("$t_2$") from the pulsed interference and reference channel output, where $R_{Jave}(t_2)$=interference channel/reference channel output for the second preselected period of time; and
   electronics configured to use $R_{Jave}(t_2)$ to determine that a calibration curve is valid for the given time period and, if the calibration curve is valid, to calculate the concentration of the targeted molecule M in the liquid sampling matrix by use of $R_{ave}(t)$ and the calibration curve and provide the concentration of the targeted molecule M in the liquid sampling matrix as an output;
   wherein the signal source emits radiation at a signal wavelength which is within a first absorption band of the targeted molecule M, the interference source emits radiation at an interference wavelength which is within a second absorption band of said at least one interfering molecule $M_J$, and the reference beam emits radiation at a reference wavelength which is neutral and is not within either the first absorption band or the second absorption band;
   wherein said at least one interfering molecule $M_J$ absorbs radiation at the signal wavelength;
   wherein the signal source, the interference source and the reference source are each pulsed at a preselected frequency of at least N Hz which is sufficiently fast so that a given molecule of the targeted molecule M or said at least one interfering molecule $M_J$ will not pass in and out of the liquid sampling matrix within the preselected frequency.

2. The apparatus of claim 1, wherein the pulsed beam is comprised of an alternate and sequential pulsing of a repeating pattern of the signal source, followed by the reference source, followed by the interference source, followed by the reference source.

3. The apparatus of claim 1, wherein the pulsed beam is comprised of an alternate and sequential pulsing of a repeating pattern of the signal source, the reference source and the interference source.

4. The apparatus of claim 1, wherein the frequency of N Hz is greater than 1.0 KHz with a duty factor of at least 10%.

5. The apparatus of claim 1, wherein t=$t_2$.

6. The apparatus of claim 1, wherein the signal beam has a signal beam center wavelength of 1,150 nm (1.150µ) and the reference beam has a center wavelength of 1,064 nm (1.064µ).

7. The apparatus of claim 6, wherein the interference beam has a center wavelength of 1,210 nm.

8. The apparatus of claim 7, wherein the targeted molecule M is glucose, said at least one interfering molecule $M_J$ is comprised of a plurality of interfering molecules contained in a body interstitial fluid and radiation emerging from the spot is collected by a lens onto the detector.

9. An apparatus for determining a concentration of a targeted molecule M within a given time period in a liquid sampling matrix in which at least one interfering molecule $M_J$ coexists with the targeted molecule, wherein the targeted molecule M is glucose and said at least one interfering molecule $M_J$ is comprised of a plurality of interfering molecules contained in a body interstitial fluid, comprising:
   a signal source;
   an interference source;
   a reference source;
   a multiplexer and a collimator configured to pulse infrared radiation from the signal source, the interference source and the reference source into a pulsed beam which is directed at an inclined angle ($\theta_i$) to a normal of a spot of the liquid sampling matrix;
   a detector configured to detect infrared radiation after it emerges from the spot as a pulsed signal and reference channel output and a pulsed interference signal and reference channel output from the pulsed beam after it penetrates into the spot and radiation emerging from the spot is collected by a lens onto the detector;
   signal processing for:
      obtaining an average ratio value of $R_{ave}(t)$ for a first preselected period of time ("t") from the pulsed signal and reference channel output, where $R_{ave}(t)$ =signal channel/reference channel output for the first preselected period of time, and obtaining an average ratio value of $R_{Jave}(t_2)$ for a second preselected period of time ("$t_2$") from the pulsed interference and reference channel output, where $R_{Jave}(t_2)$=interference channel/reference channel output for the second preselected period of time; and electronics configured to use $R_{Jave}(t_2)$ to determine that a calibration curve is valid for the given time period and, if the calibration curve is valid, to calculate the concentration of the targeted molecule M in the liquid sampling matrix by use of $R_{ave}(t)$ and the calibration curve and provide the concentration of the targeted molecule M in the liquid sampling matrix as an output;

wherein the signal source emits radiation which has a signal beam center wavelength of 1,150 nm (1.150µ), the interference source emits radiation which has a center wavelength of 1,210 nm, and the reference beam emits radiation which has a center wavelength of 1,064 nm (1.064µ);

wherein said at least one interfering molecule $M_J$ absorbs radiation at the signal wavelength;

wherein the signal source, the interference source and the reference source are each pulsed at a preselected frequency of at least N Hz which is greater than 1.0 KHz with a duty factor of at least 10% and is sufficiently fast so that a given molecule of the targeted molecule M or said at least one interfering molecule $M_J$ will not pass in and out of the liquid sampling matrix within the preselected frequency.

10. The apparatus of claim 9, wherein the pulsed beam is comprised of an alternate and sequential pulsing of a repeating pattern of the signal source, followed by the reference source, followed by the interference source, followed by the reference source.

11. The apparatus of claim 9, wherein the pulsed beam is comprised of an alternate and sequential pulsing of a repeating pattern of the signal source, the reference source and the interference source.

12. The apparatus of claim 9, wherein $t=t_2$.

* * * * *